US00PP10569P

United States Patent [19]

Potgieter

[11] Patent Number: Plant 10,569

[45] Date of Patent: Aug. 25, 1998

[54] CANNA PLANT NAMED 'PHASION'

[76] Inventor: Jan H. Potgieter, P.O. Box 536, Bethal 2310, South Africa

[21] Appl. No.: 709,533

[22] Filed: Sep. 6, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 9,154 6/1995 Roberson ..... Plt./68.1
P.P. 9,896 5/1997 Roberson ..... Plt./68.1

OTHER PUBLICATIONS

GTITM UPOV ROM Listing PBR HOM 049, 1995.
GTITM UPOV ROM Listing PBR 95158, 1995.

*Primary Examiner*—James R. Feyrer
*Assistant Examiner*—Kent L. Bell
*Attorney, Agent, or Firm*—Foley & Lardner

[57] ABSTRACT

A new and distinct cultivar of canna plant named 'Phasion', characterized particularly by the wide variance in color of the interveinal striping of the leaves as they age, with the striping being a deep greyed-purple on new leaves, maturing through a deep green with an infusion of greyed-purple, to a lighter green, with the midrib and minor veins changing from an orange-red to a much more yellow orange and orange, respectively, with leaf maturity. A plant with leaves of various age produces a spectacular display of varying colors.

3 Drawing Sheets

1

The present invention comprises a new and distinct cultivar of canna, botanically known as *Canna hybrida*, and referred to by the cultivar name 'Phasion'.

The new cultivar was discovered by the inventor Jan H. Potgieter in Bethal, South Africa and resulted from the open pollination of Canna 'Wyoming'. The new cultivar was selected from the progeny by the inventor in Bethal, South Africa with the selection being primarily due to the unique leaf color of the new cultivar. The multiple striped leaves display coloring, at various stages of maturity, of pink, red, carmine, green, yellow, burgundy, very deep greyed-purple, and orange, a truly unique combination of colors.

The first act of asexual reproduction of 'Phasion' was accomplished when rhizomes were split off from the initial selection by the inventor in a controlled environment in Bethal, South Africa.

Horticultural examination and comparative trials of successive plantings conducted both at Bethal, South Africa and Silvan, Victoria, Australia, have shown that the unique combination of characteristics as herein disclosed for 'Phasion' are firmly fixed and are retained through successive generations of asexual reproduction.

'Pink Phasion' has not been observed under all possible environmental conditions. The phenotype may vary significantly with variations in environment such as temperature, light intensity and daylength without, however, any variation in genotype.

The following observations, measurements, and comparisons describe plants grown in Silvan, Victoria, Australia, under conditions which approximate those generally used in commercial practice.

The new cultivar is primarily distinguished from its parent and also from other hybrid cultivars of the genus by the multiple striped or interveinal coloring of its leaves, and its orange to yellow orange midrib and vein. Leaf colors include pink, red carmine, green, yellow, orange and burgundy, depending on leaf maturity. By contrast, the leaves of 'Wyoming' are a uniform medium dark green with greyed-purple midrib and veins. The interveinal stripes of 'Phasion' begin at the base of each leaf and extend outwardly toward the edges or tips of the leaves, with the shape and color of the stripes being irregular. The leaves provide a vivid contrast with the rich orange flowers.

2

In addition to leaf color, the new cultivar 'Phasion' is distinguished from 'Wyoming' by its significantly shorter plant height, medium size and slow growth rate, shorter and narrower leaves, and its shorter flower stems.

The accompanying color photographs show the unique colors of the leaves as closely as possible with illustrations of this type.

The photograph on sheet 1 is a top perspective view of a typical specimen plant of 'Phasion', illustrating leaves of varying maturity and capturing the full panoply of leaf color.

The photograph on sheet 2 illustrates leaves predominantly intermediate in age and color, and a single open bloom.

The photo on sheet 3 is a closeup view of two leaves generally intermediate in maturity.

In the following description, color references are made to The Royal Horticultural Society Colour Chart. The color values were determined on plant material grown in ambient outdoor conditions at Silvan, Victoria, Australia.

Plant

Type: Slow growing rhizomatous herb.

Height: Approximately 75–80 cm, relatively short compared to other cultivars.

Growth habit and rate: Upright growth habit; medium in size; growth rate is slow.

Roots: Rhizomes are well developed and about 1.5 cm in diameter; internodes 1 cm; rhizomes are covered in scale which darkens to brownish black on maturity; fleshy roots mainly at base of plant, color 65 C.

Leaves:

*Arranged.*—Spirally.

*Shape.*—Lamina large, ovate to broad elliptic, entire and multicolored.

*Length.*—Average approximately 40 cm.

*Width.*—Average 20–22 cm at widest area.

*Color.*—It is impossible to capture all of the many colors of the leaves as they mature from a new or young condition just opening to a fully mature condition. The photo on sheet 1 reasonably closely depicts true leaf color for new and older leaves as stated below by color value, and also shows numerous leaves at various stages of maturity. A plethora of colors are present, the totality of which produces a spectacular result. New leaves generally described are dark greyed-purple between veins, with the midribs and smaller veins being an orange-red. A new leaf generally depicting these values is shown at the bottom center of the photo on sheet 1. Relatively old or mature leaves are generally described as having medium to dark green color in the prominent interveinal or striped areas, a lighter yellow-orange midrib, and medium orange veins. A reasonably close depiction of those mature color values appear in the right-most leaf in the photo on sheet 1.

Between the new and old color extremes, the leaves go through a myriad of color changes, as shown particularly in the photograph on sheet 1. As the leaves mature to full size, the interveinal color changes from deep greyed-purple to a deep green infused with purple (see photos on sheets 2 and 3), changing to a lighter green as the leaves fully age. The midrib and veins maintain their orange-red color (see photo on sheet 3) as the leaves reach full size, with the midrib becoming a much lighter yellow-orange and the minor veins a lighter orange as the leaves turn older. It is not practical to provide values for the multitude of colors as the leaves mature, thus the listing of the color values for only new and old leaves. However, the full range of color is shown in the photo on sheet 1.

*Interveinal zones.*—187A-B on new leaves and 146A-B on older leaves.

*Midrib.*—Prominent, 34A, changing to 19A on older leaves

*Minor veins.*—34A on new leaves, changing to 26B on older leaves.

Inflorescence

General: Inflorescence is a terminal raceme about 30–45 cm long, almost branching to second main axis which may be as large as main axis; main axis always flowers before secondary axis; bracteate, with upper bracts subtending solitary or parred sessile or very short pedicellate flowers. Flowering time is Spring to Autumn.

*Flower shape and color.*—Flowers are bisexual, asymmetric and showy, and are about 130 mm across; color generally yellow orange with veins having upper surface color closest to R.H.S. 28A, and lower surface closest to 28B; interveinal areas are closest to 17A.

*Sepals.*—Three (3) in number, overlapping, free, equal, 28C in color.

*Petals.*—Three (3) uequal, united in basal tube.

*Reproductive organs.*—Single stamen is petaloid with solitary marginal anther, united to fleshy style; staminodes are two in number with one almost as big as petal and same color, recurved; nectarial glands present; ovary inferior, 3-locular, verrucose, ovules numerous, style petaloid, 28A in color.

*Fruit.*—Not fully developed, verrucose, capsule, color greenish with red-purple tinge; seed do not develop.

Disease resistance:

The new cultivar has not shown any abnormal susceptibility to diseases or insects most commonly encountered in the cultivation of this species.

I claim:

1. A new and distinct canna plant name 'Phasion', as illustrated and described.

* * * * *

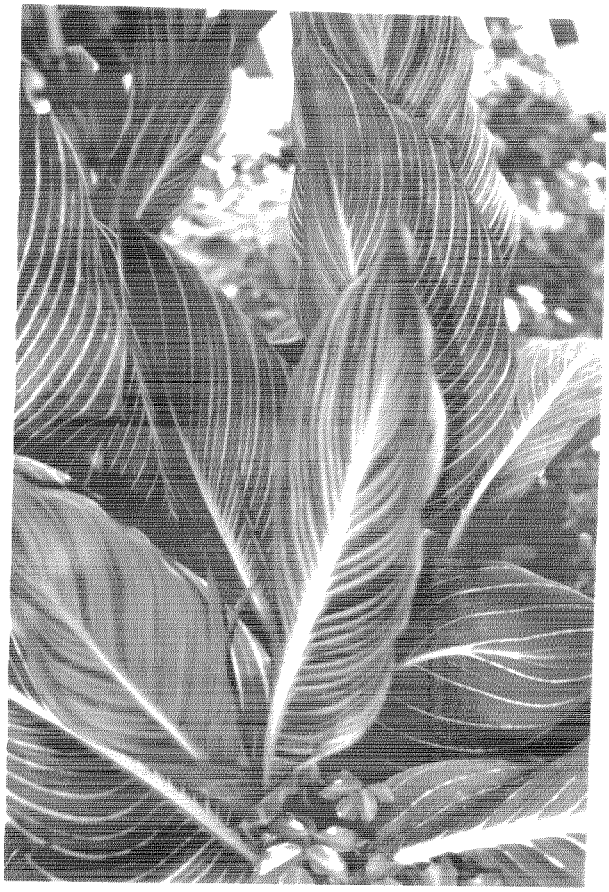

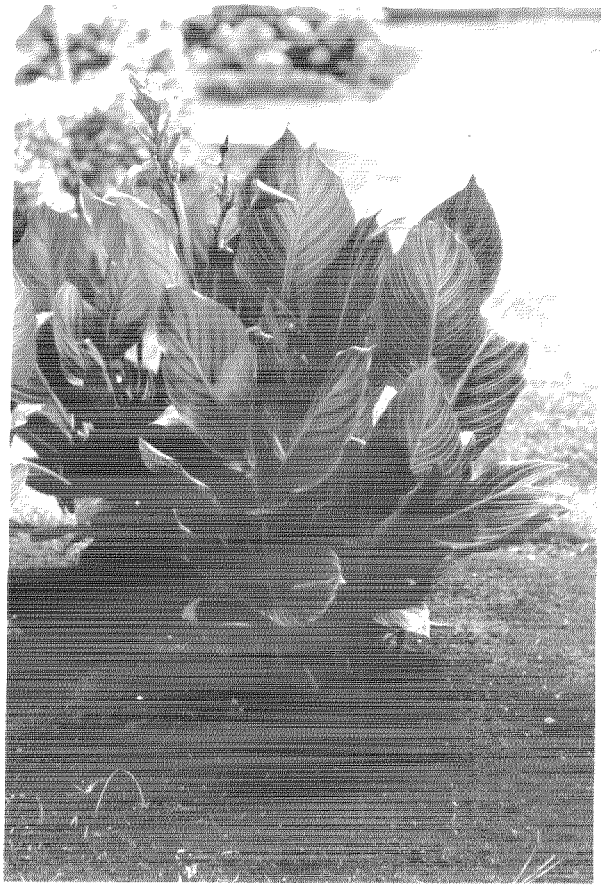

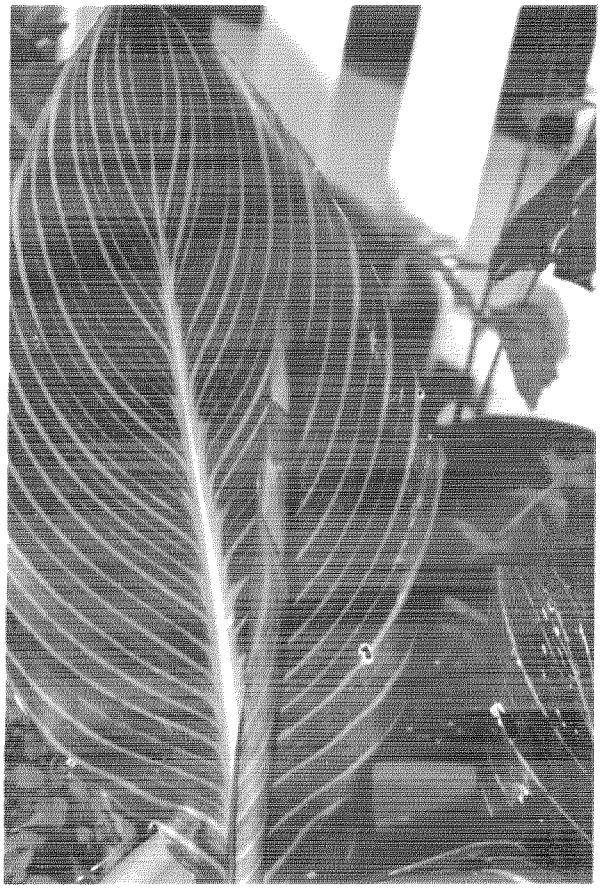

UNITED STATES PATENT AND TRADEMARK OFFICE

CERTIFICATE OF CORRECTION

PATENT NO. : PP 10,569
DATED : August 25, 1998
INVENTOR(S) : Jan H. Potgieter

It is certified that error appears in the above-identified patent and that said Letters Patent is hereby corrected as shown below:

Title page,
Line 24, under the subheading entitled 'Plant', please change "75-80 cm" to -- 1.2 to 2.0 meters --.

Signed and Sealed this

Eighteenth Day of June, 2002

*Attest:*

*Attesting Officer*

JAMES E. ROGAN
*Director of the United States Patent and Trademark Office*